United States Patent
Korn

(10) Patent No.: US 11,120,888 B2
(45) Date of Patent: Sep. 14, 2021

(54) SYSTEMS AND METHODS FOR PREDICTING LUNG CANCER IMMUNE THERAPY RESPONSIVENESS USING QUANTITATIVE TEXTURAL ANALYSIS

(71) Applicant: Imaging Endpoints II LLC, Scottsdale, AZ (US)

(72) Inventor: Ronald L. Korn, Paradise Valley, AZ (US)

(73) Assignee: IMAGING ENDPOINTS II LLC, Scottsdale, AZ (US)

(*) Notice: Subject to any disclaimer, the term of this patent is extended or adjusted under 35 U.S.C. 154(b) by 617 days.

(21) Appl. No.: 15/237,530

(22) Filed: Aug. 15, 2016

(65) Prior Publication Data

US 2018/0046750 A1     Feb. 15, 2018

(51) Int. Cl.
| | | |
|---|---|---|
| *G16B 5/00* | (2019.01) | |
| *G16B 40/00* | (2019.01) | |
| *G16B 20/00* | (2019.01) | |

(52) U.S. Cl.
CPC ............. *G16B 5/00* (2019.02); *G16B 20/00* (2019.02); *G16B 40/00* (2019.02)

(58) Field of Classification Search
None
See application file for complete search history.

(56) References Cited

U.S. PATENT DOCUMENTS

| | | |
|---|---|---|
| 7,769,423 B2 | 8/2010 | Viglianti |
| 9,092,691 B1 | 7/2015 | Beaumont |
| 9,304,973 B2 | 4/2016 | Heine |
| 2010/0142775 A1 | 6/2010 | Ganeshan |
| 2010/0266179 A1 | 10/2010 | Ramsay |
| 2014/0233826 A1 | 8/2014 | Agaian |

FOREIGN PATENT DOCUMENTS

| | | |
|---|---|---|
| WO | 2012125411 A1 | 9/2012 |
| WO | 2014097124 A2 | 6/2014 |

OTHER PUBLICATIONS

International Searching Authority. International Search Report and Written Opinion for application PCT/US2017/047026. dated Nov. 22, 2017. 12 pages.
Ganeshan, B., et al. "Non—small cell lung cancer: histopathologic correlates for texture parameters at CT." Radiology 266.1 (2013): 326-336.
De Cecco, C. N., et al. "Texture analysis as imaging biomarker of tumoral response to neoadjuvant chemoradiotherapy in rectal cancer patients studied with 3-T magnetic resonance." Investigative radiology 50.4 (2015): 239-245.

*Primary Examiner* — G Steven Vanni
(74) *Attorney, Agent, or Firm* — Quarles & Brady LLP

(57) ABSTRACT

Methods and apparatus for predicting responsiveness to immune therapy in lung cancer. The method includes the steps of: identifying a first population of known responders and a second population of known non-responders; processing imaging data for the first and second populations using quantitative textural analysis (QTA); generating, for each member of both populations, quantitative metrics using the QTA; performing logistic regression on the quantitative metrics for both populations to yield a predictive signature expressed in the form of Y=Mx+B where x comprises mean pixel density; performing QTA on a lung cancer scan for a subsequent patient; comparing the predictive signature to one or more relevant metrics associated with the subsequent patient; and predicting responsiveness to immune therapy for the subsequent patient based on the comparison.

20 Claims, 7 Drawing Sheets

Analysis Results

| Image | Roiid | Roiname | SSF | TX_sigma | mean | sd | entropy | mpp | skewness | Kurtosis | total | algorithm |
|---|---|---|---|---|---|---|---|---|---|---|---|---|
| CRT79 | 0 | ROI_0 | 2 | 1.05 | -7.92 | 63.17 | 4.64644 | 48.6094 | 0.5589 | 0.934 | 146 | Lung |
| CRT79 | 0 | ROI_0 | 4 | 2.1 | -0.89 | 30.02 | 3.80365 | 24.7941 | 0.4229 | -0.4565 | 71 | Lung |
| CRT79 | 0 | ROI_0 | 6 | 3.15 | 5.46 | 11.57 | 3.00477 | 11.6176 | -0.5554 | -0.6241 | 24 | Lung |
| CRT79 | 0 | ROI_0 | 0 | 0 | 44.58 | 51.58 | 4.80659 | 60.0727 | 0.6301 | 0.4169 | 271 | Lung |
| CRT79 | 0 | ROI_0 | 3 | 1.58 | -7.64 | 29.3 | 3.83435 | 23.7692 | 0.655 | 0.1198 | 71 | Lung |
| CRT79 | 0 | ROI_0 | 5 | 2.63 | 0.67 | 15.37 | 2.77372 | 13.4167 | -0.1835 | -0.6521 | 24 | Lung |

FIG. 3

Multiple Regression y=.4546 + .007114 ✳ → Mean

| Dependent Y | Respnse |
|---|---|

Least Squares Multiple Regression

| Method | Forward |
|---|---|
| Enter Variable if P< | 0.05 |
| Remove Variable if P> | 0.1 |

| Sample Size | 14 |
|---|---|
| Coefficient of Determination $R^2$ | 0.3224 |
| $R^2$-Adjusted | 0.2659 |
| Multiple Correlation Coefficient | 0.5678 |
| Residual Standard Deviation | 0.4400 |

Regression Equation

| Independent Variables | Coefficient | Std. Error | $r_{partial}$ | t | P |
|---|---|---|---|---|---|
| (Constant) | 0.4546 | | | | |
| Mean | 0.007114 | 0.002977 | 0.5678 | 2.390 | 0.0342 |

| Variables not Included in the Model |
|---|
| Entropy |
| Kurtosis |
| MPP |
| Sd |
| Skewness |

Analysis of Variance

| Source | DF | Sum of Squares | Mean Square |
|---|---|---|---|
| Regression | 1 | 1.1054 | 1.1054 |
| Residual | 12 | 2.3232 | 0.1936 |

| F-Ratio | 5.7099 |
|---|---|
| Significance Level | P=0.0342 |

FIG.6

Multiple Regression  $y = .5211 + .008576 \cdot \leftarrow \rightarrow$ Mean Using $SSF_3$

| Dependent Y | Responders |
|---|---|
|  | Responders |

Least Squares Multiple Regression

| Method | Forward |
|---|---|
| Enter Variable if P< | 0.05 |
| Remove Variable if P> | 0.1 |

| Sample Size | 32 |
|---|---|
| Coefficient of Determination $R^2$ | 0.2889 |
| $R^2$-Adjusted | 0.2652 |
| Multiple Correlation Coefficient | 0.5375 |
| Residual Standard Deviation | 0.4216 |

Regression Equation

| Independent Variables | Coefficient | Std. Error | $r_{partial}$ | t | P |
|---|---|---|---|---|---|
| (Constant) | 0.5211 |  |  |  |  |
| Mean | 0.008576 | 0.002456 | 0.5375 | 3.491 | 0.0015 |

| Variables not Included in the Model |
|---|
| Entropy |
| Kurtosis |
| MPP |
| Sd |
| Skewness |

Analysis of Variance

| Source | DF | Sum of Squares | Mean Square |
|---|---|---|---|
| Regression | 1 | 2.1668 | 2.1668 |
| Residual | 30 | 5.3332 | 0.1778 |

| F-Ratio | 12.1886 |
|---|---|
| Significance Level | P=0.0015 |

FIG.7

SYSTEMS AND METHODS FOR PREDICTING LUNG CANCER IMMUNE THERAPY RESPONSIVENESS USING QUANTITATIVE TEXTURAL ANALYSIS

TECHNICAL FIELD

The present invention relates, generally, to a biomarker signature for predicting whether a lung cancer patient will respond to immune therapy and, more particularly, to systems and methods for deriving the signature from imaging data using quantitative textural analysis.

BACKGROUND

Immune therapy broadly contemplates administering a drug which provokes the immune system to attach cancer cells, rather than attacking the cancer cells directly. Characterizing lesion biology is an important component in effective immunotherapy treatment. Presently known methodologies for evaluating tumor biology involve invasive tissue analysis and the attendant delay (e.g., weeks) in obtaining interpretable results. A non-invasive alternative that provides a real-time analysis of lung cancer tumors is thus needed.

An evolving strategy for the non-invasive interrogation of tumors involves analyzing diagnostic images to identify patterns of appearances that are linked to tumor biology, such as tumor enhancement on cross sectional imaging as a surrogate for tumor angiogenesis, fluorodeoxyglucose positron emission tomography (FDG PET) for tumor metabolism, and the like. Imaging analysis provides a non-invasive, low risk approach to assessing tumor biology prior to therapy and an objective pathway for monitoring immunotherapy response.

Using signals detected on cross sectional imaging to characterize tumor biology is based on several factors including: (1) tumors images express underlying tumor biology; (2) growth kinetics and other drivers of oncologic transformation may have unique expression patterns on imaging; (3) unique expression patterns can manifest themselves as imaging phenotypes; and (4) the imaging phenotypes can be characterized both qualitatively and quantitatively. Thus, an understanding of disease biology can be derived, measured, inferred or predicted by examining the imaging phenotype or appearance of a tumor by different radiologic means. This coupled with imaging's ability to provide a comprehensive and real-time assessment of the entire tumor and its micro-environment make quantitative imaging an attractive tool for rapid assessment and prognosis.

Qualitative descriptions of the appearance of tumors on imaging can provide some degree of biologic characterization but are open to interpretation and lack standardization and reproducibility. For example, descriptions of spiculated margins of a mass can infer both an assessment of the malignant nature of the lesion and the provocation of surrounding fibrosis by the tumor and, when present, is a reliable marker of malignant desmoplastic responses. On the other hand, lesions with an ill-defined or irregular margin are less specific for malignancy or its underlying biology. Although there is general agreement on many qualitative descriptors, reader variability can be broad. Thus, being able to take qualitative features and perform quantitative analysis on imaging is appealing. For example, quantitative analysis of spiculation could provide a more standardized, objective, reliable and predictable measure of a lesion's appearance and biologic behavior.

Presently known techniques for quantifying tumor properties on imaging either utilize special imaging technologies (e.g., perfusion and diffusion weighted MM images, FDG metabolism on PET) with the measurement of specific parameters (such as Ktrans, ADC, SUV) or comprise superficial markers with limited verifiable connection to biology (e.g., size or volume measurements of tumor lesions). Recently, leading scientists from University College in London (UCL) have developed a software platform known as TexRAD that provides quantitative measurements (referred to herein as Quantitative Textural Analysis or QTA) of tumor lesions based primarily on CT images. In this context, computed tomography (CT) and computerized axial tomography (CAT) scans make use of computer-processed combinations of many X-ray images taken from different angles to produce cross-sectional (tomographic) images (virtual "slices") of the organ under inspection.

QTA is a post-processing technique that can be used to quantify tissue complexity by assessing the distribution of textural features (or heterogeneity) within a tumor lesion and their change following treatment. Studies have shown that tumor complexity is seen in multiple imaging modalities and can be derived from many different image types, sequences or imaging series (e.g. CT, MRI, PET, and Mammography). Further work has shown that individual parameters of tumor complexity measured on QTA can reflect the biologic signals of hypoxia, intratumoral vascular shunting and perfusion.

Tumor complexity can be quantified by QTA using a range of measurable parameters based on enhancement characteristics and/or density changes on a local level by clustering small groups of pixels together using filter kernels (referred to as spatial scale filters (SSF) within a lesion itself. The output from the analysis then provides a measure of tumor heterogeneity. However, much of the heterogeneity visible on CT can represent photon noise, which tends to mask or suppress the signal strength of underlying biologic information. By first filtering out the noise, QTA analysis can then be used to more effectively probe the biological diversity inherent in tumor complexity. For example, Ganeshan et al (Radiology 2013; 266: 326-36) have noted correlations of QTA parameters with tumor hypoxia in lung cancer, Kras mutations in colorectal cancer and tumor grade in gliomas.

Notwithstanding the potential for QTA as a tool for finding imaging biomarkers, a reliable signature for predicting responsiveness to immune therapy in lung cancers remains elusive.

Methods and apparatus are thus needed which overcome the limitations of the prior art.

Various features and characteristics will also become apparent from the subsequent detailed description and the appended claims, taken in conjunction with the accompanying drawings and this background section.

BRIEF SUMMARY

The present invention provides a biomarker signature for predicting immune therapy responsiveness in lung cancer patients. The signature is derived from aggregate imaging data in conjunction with quantitative textural analysis (QTA) and logistic regression modeling techniques. Various embodiments involve: i) unambiguously identifying a first population of known responders and a second population of known non-responders; ii) processing conventional imaging data (e.g., CT scan data) for both populations using a quantitative textural analysis (QTA) platform; iii) generating, for both populations, respective histograms and related quantitative metrics such as mean pixel density, standard deviation of the histogram curve, mean positive pixel value of the pixels that are in the positive value range, entropy, skewness, and kurtosis of the curves; iv) performing logistic regression on the quantitative metrics for both populations to yield a model predictive signature; v) performing QTA on subsequent lung cancer patients; vi) comparing the signature to one or more relevant metrics for the subsequent patients; and vii) predicting responsiveness to immune therapy for individual patients based on the comparison.

Imaging modalities such as CT, analytical techniques such as QTA, and logistic regression algorithms are powerful tools; yet they are only tools. By themselves, they do not advance cures. Rather, the ingenuity, creativity, commitment, and passion—in short, the inspiration and perspiration of human researchers—must ultimately be brought to bear on these technologies. The foregoing analytical tools are employed by the cancer researcher just as the chisel and rasp are used by the sculptor to coax a work of art out of a slab of marble. The present inventor has successfully employed QTA and logistic regression techniques on aggregate imaging data for unambiguously known responders and unambiguously known non-responders to develop a statistically reliable signature for predicting responsiveness to immune therapy for lung cancers.

It should be noted that the various inventions described herein, while illustrated in the context of CT image data, are not so limited. Those skilled in the art will appreciate that the inventions described herein may contemplate any scanning modality, including but not limited to MRI, US, PAT, DEXA, digital mammography, JPEGS, Angiography, SPECT, gamma cameras, and other optical platforms.

Various other embodiments, aspects, and features are described in greater detail below.

BRIEF DESCRIPTION OF THE DRAWING FIGURES

Exemplary embodiments will hereinafter be described in conjunction with the appended drawing figures, wherein like numerals denote like elements, and:

FIG. 3 is an exemplary data matrix corresponding to the histogram of FIG. 2 in accordance with various embodiments;

FIG. 6 is a first exemplary multiple regression output table in accordance with various embodiments; and FIG. 7 is an alternate exemplary multiple regression output table in accordance with various embodiments.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to methods for developing a biomarker signature for predicting immune therapy responsiveness in lung cancers, including the steps of: i) obtaining cross sectional images from CT, MRI, US, PET, DEXA, Digital Mammography, JPEGS, Angiography, SPECT, gamma cameras, and/or optical platforms; ii) loading the imaging data into a suitable QTA platform (e.g., TexRAD) and selecting a region of interest (ROI) surrounding the tumor in the form of a rectangle, Ellipse, polygon, seed point, or other region encompassing the tumor; iii) selecting either a single slice or multiple slices for QTA; iv) selecting an appropriate filter algorithm (e.g., Liver, Lung, Mammo general, Mammo fine); v) filtering the pixels to a single common size and shape and clustering them together as nearest neighbors into groups of 2, 3, 4, 5, and 6 pixels each representing SSFs of 0 (no filter), 2 (fine), 3-4 (moderate), and 5-6 (coarse); vi) applying the different SSFs to the ROI area pixels and generating a histograph frequency curve for each SSF; vii) deconstructing each curve to yield metrics representing, for example, mean pixel density, standard deviation of the histogram curve, mean positive pixel value of the pixels that are in the positive value range, entropy, skewness, and kurtosis; viii) displaying the values in a matrix or otherwise representing the values in the form of equations; viii) performing logistic regression on the matrix values; and ix) using the results of the logistic regression individually or in combination with other clinical, laboratory, imaging, demographic, or other bio-informatic measurements to create imaging phenotypes for further connectivity to a predicted outcome.

Figure 1:
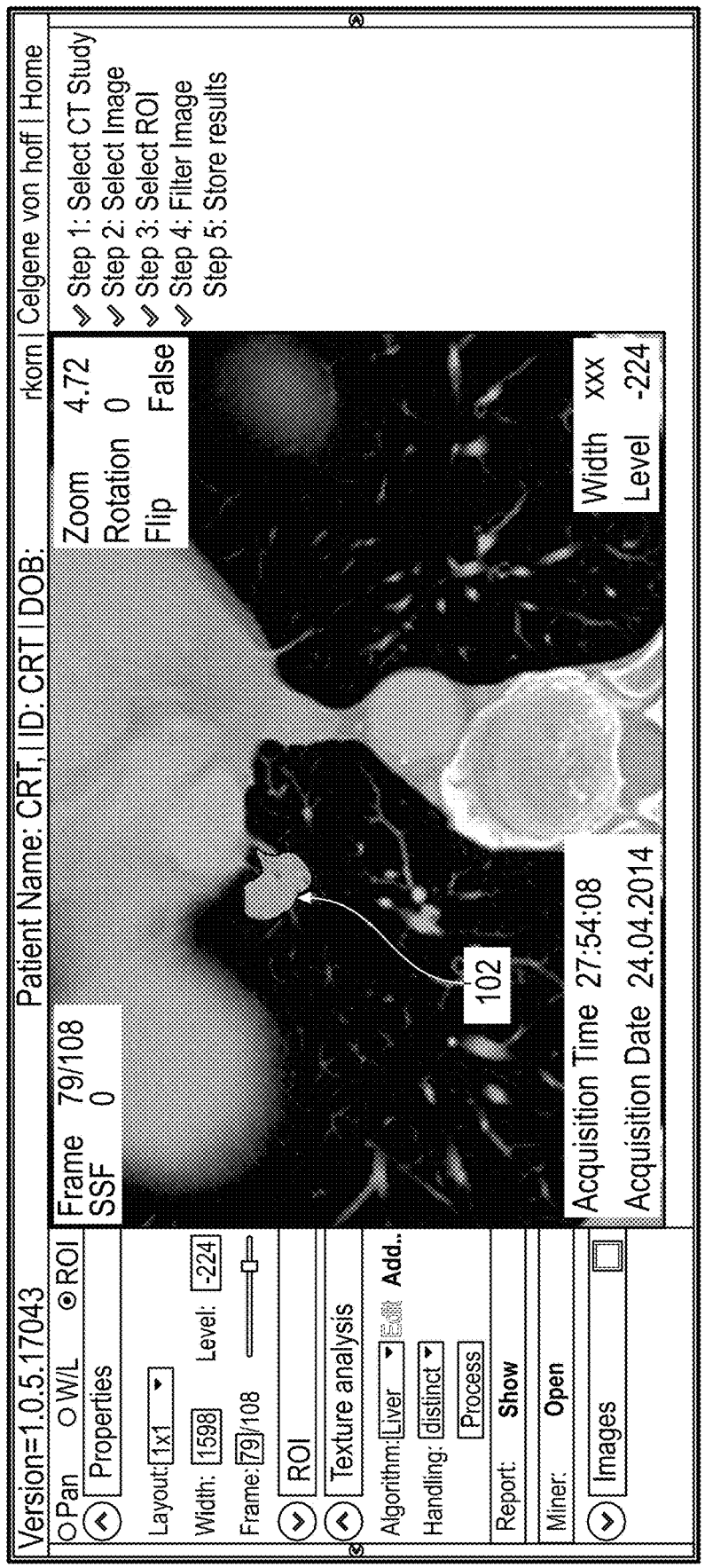
FIG. 1 is an exemplary CT scan slice illustrating a region of interest (ROI) in accordance with various embodiments.

In a preferred embodiment, a volumetric CT imaging data set for each of a plurality of lung cancer tumors is analyzed. Referring now to FIG. 1, for each slice 100 in each data set, a region of interest (ROI) 102 is identified (typically manually). For each data set, an optimum slice is selected for further processing, such as the most heterogeneous, irregular slice from the data set. Alternatively, the entire data set or a subset thereof may be employed.

For the selected slice, the pixels within the ROI 102 are processed using QTA. An initial processing step involves selecting, an appropriate filter based on thresholds of density, with air being the least dense and bone being the most dense. That is, the filter seeks to remove air and bone pixels, leaving only pixels within the ROI of biological relevance.

Figure 2:
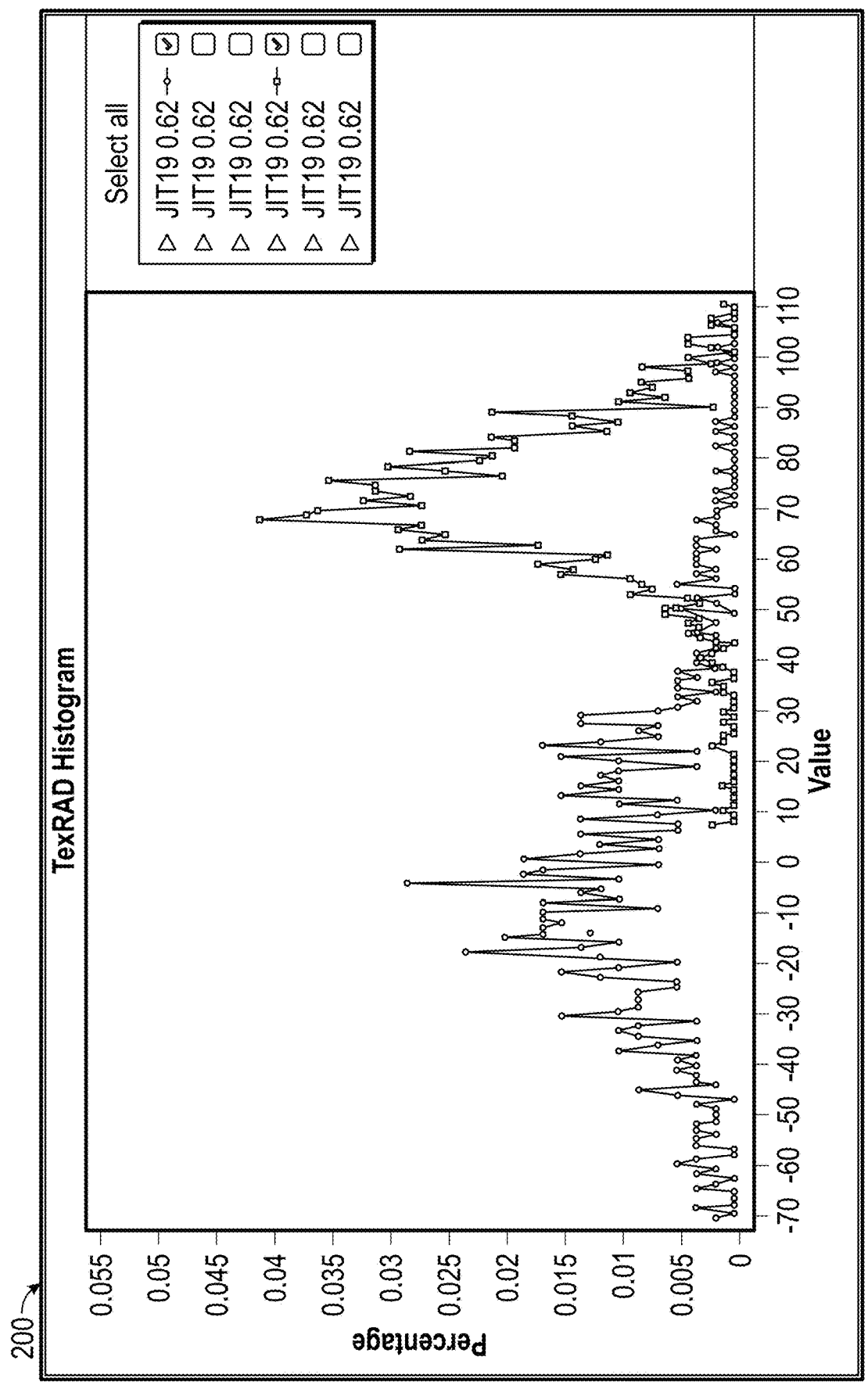
FIG. 2 is an exemplary histogram curve in accordance with various embodiments.

Referring now to FIG. 2, the ATQ platform then generates a histogram 200 of the frequencies of occurrence (Y-axis) of pixels within discrete density boundaries (X-axis). CT images typically display greyscale values in terms of Hounsfield units, where water=0 in a scale from −1500 to +1500. Pixels more dense than water are positive; pixels less dense than water have negative values. Density values may be generally grouped into four tissue types that exhibit contrast: air (less than −80); fat (−80 to −20); water/soft tissue (−20 to 300); and bone (above 300). After applying a selected band pass filter to remove the very high and very low density pixels, a histogram is generated upon which the following calculations and statistical analyses are performed.

Referring now to FIG. 3, the system (e.g., TexRAD) then calculates various metrics for one or more spatial scale filter (SSF) filter values 301 associated with the histogram, including: i) the mean pixel value 302 representing the average density within a cluster of pixels at a given SSF level; ii) the standard deviation (SD) 304 which is a measure of tumor heterogeneity and microstructural change; iii) entropy 306 representing the mean density of clustered pixels over the entire ROI area (Ln [mean density/total pixels]) and is based on different filtering parameters that are reflective of tumor homo/heterogeneity; iv) mean positive pixel (mpp) value 308, sometimes regarded as a measure of hypoxia; v) skewness 310 used to measure the symmetry of contrast distribution in regions of interest, where skewness is measured by the slant of the peak either to the right (negative skewness) or to the left (positive skewness); vi) kurtosis 312 which is determined by the height of the histogram and regarded as a measure of tumor angiogenesis, vascular shunting and/or tumor homogeneity; and vii) the total pixel number 314 for the histogram.

Figure 4:
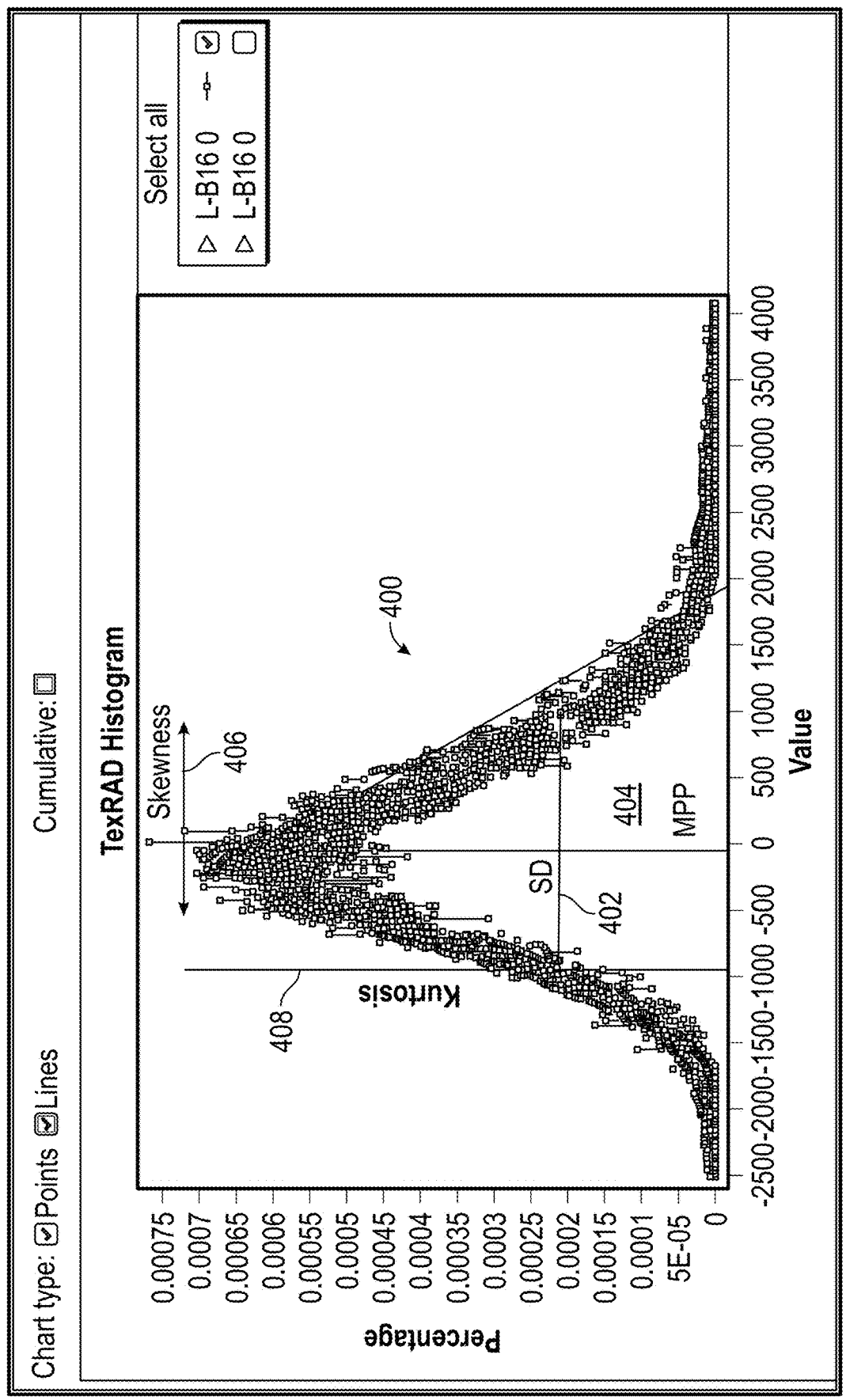
FIG. 4 is an exemplary histogram illustrating quantitative metrics in accordance with various embodiments.

The foregoing histogram and the associated metrics embody biological information, which the present inventor seeks to harness in the form of a signature useful in predicting responsiveness to immune therapy for lung cancer. Specifically, the present inventor seeks to characterize the data in terms of a signature against which future patient scans may be evaluated to predict responsiveness to immune therapy with a high degree of confidence. FIG. 4 illustrates a histogram 400 and graphically depicts the following exemplary metrics: standard deviation 402; mpp 404; skewness 406; and kurtosis 408.

In this regard, immune therapy broadly involves using drugs to provoke the immune system to attack the cancer, rather than using drugs to attack the cancer directly. Immune therapy works well in approximately 30% of patients, but is quite expensive (e.g., $25,000/month). In approximately 70% of patients immune therapy helps only a little or not at all. It is therefore desirable to predict in advance whether a particular patient is likely to respond to immune therapy, based on comparison to a signature previously derived from a population known to respond to immune therapy.

After evaluating each SSF filter level (corresponding to 0, 2, 3, 4, 5, or 6 adjacent clustered pixels) independently, the associated metric values may be summarized in a matrix as shown in FIG. 3, which represents a deconstructed histogram for the pixels within an ROI of a single slice for a single patient for various SSF values.

The foregoing metrics may then be processed using a simple T-test to determine whether a difference between respective mean values for two population groups (e.g., responder and non-responder) is unlikely to have occurred because of random chance in sample selection. Each metric having a significant difference between the average value for the responder population and the average value for the non-responder population is a good candidate for including in the signature.

A more robust signature may be derived using logistic regression to yield a signature representative of the underlying biology, where metrics which influence the outcome (immune therapy responder or non-responder) are preserved in the model, and where metrics which do not influence the outcome are not preserved in the model. More particularly, known responders are allocated a 1 and known non-responders are allocated a zero, where zero and 1 are the dependent variables in the logistic regression analysis. The logistic regression model then reveals the principal factors that align with responders/non-responders, as well as their coefficients. This can be done using forward, backward, step wise, or any other desired statistical protocol.

In an embodiment, the logistic regression analysis employs a matrix of equations of the form $1=Ax_1+Bx_2+Cx_3+Dx_4+Ex_5+Fx_6$ for responders, and of the form $0=Ax_1+Bx_2+Cx_3+Dx_4+Ex_5+Fx_6$ for non-responders, where $x_1$ corresponds to the mean, $x_2$ corresponds to the standard deviation, $x_3$ corresponds to entropy, $x_4$ corresponds to mpp, $x_5$ corresponds to skewness, and $x_6$ corresponds to kurtosis. The logistic regression analysis then determines which metrics influence immune therapy responsiveness, and calculates the associated coefficients (e.g., A-F) for the metrics retained in the model.

In an alternate embodiment, one or more extra columns may be used in addition to the aforementioned metrics to enhance the predictive value of the signature. This additional column or columns may relate to bio-informatic metrics such as, for example, smoking history, gene mutation load, tumor markers, pathology information (age, gender); logistic regression analysis may then be performed on all columns.

The logistic regression process, which may be implemented in an algorithm, produces a master equation using well known techniques, and retains the statistically important independent variables and discards the statistically unimportant independent variables. A binary logistic model may be used to estimate the probability of a binary response based on one or more predictor (or independent) variables (features).

Figure 5:
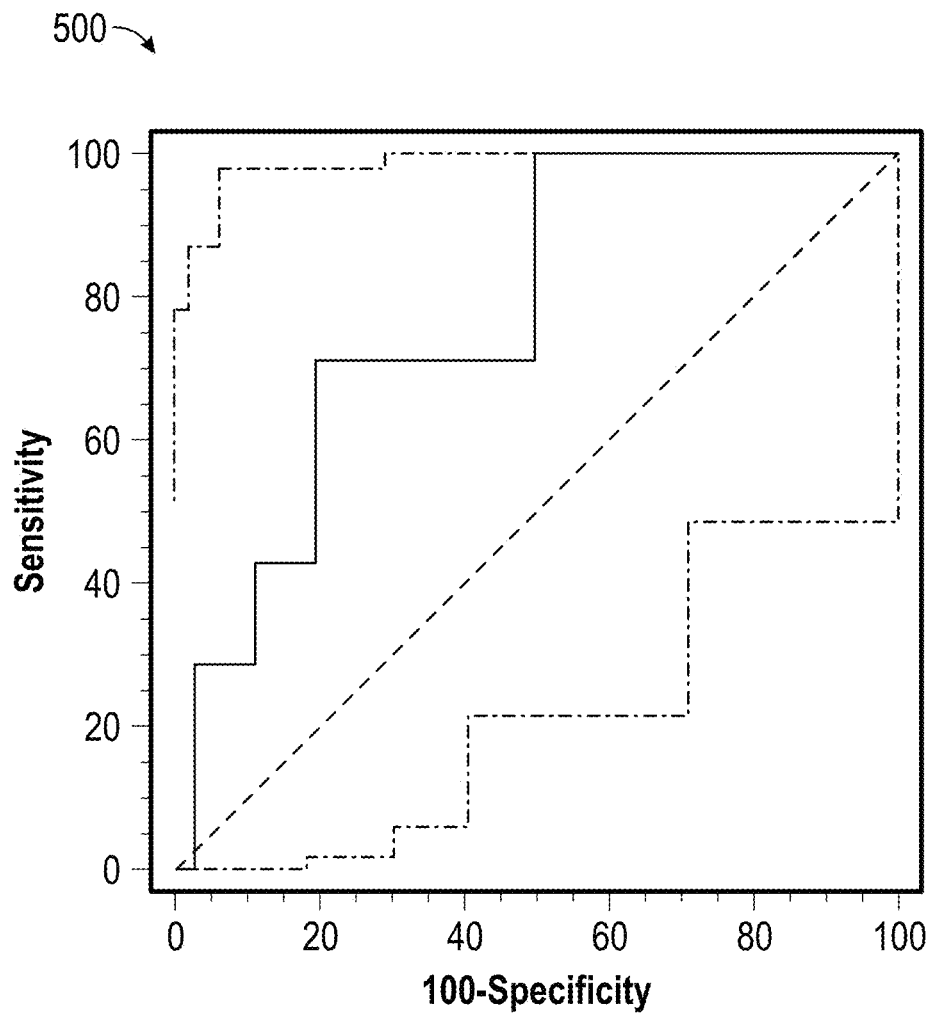
FIG. 5 is an exemplary receiver operator characteristics (ROC) curve in accordance with various embodiments.

Once a preliminary logistic regression analysis has been performed and one or more metrics are identified as significant, they may be expressed as an equation of the form $1=Ax+By+Cz$, where x, y, and z are the metrics determined to be linked to the responder outcome, and A, B, and C are their corresponding coefficients (at least one of which is non-zero). With momentary reference to FIG. 5, this equation may then be expressed as a receiver operator characteristics (ROC) curve 500 and analyzed to determine the cut-off value which yields the highest sensitivity. For example, by inspecting an exemplary receiver operator characteristics curve, one may conclude that if x, y, and/or z exceed predetermined threshold values, the patient is statistically likely to be a responder.

Once a linkage is established between responders and the metrics retained in the logistic regression model, the linkage is preferably validated before declaring the signature statistically stable. That is, if a new candidate is determined to be a responder based on comparison of that patient's scan metrics to the signature, we then follow up to confirm that he does in fact respond. If he does not respond when predicted to do so, the reasons underlying the discrepancy are addressed or the signature revised. Once the signature is positively validated, the validated signature becomes the predictive test we know to a statistical certainty that declared responders will in fact respond.

The results of a first logistic regression analysis using a sample size of 14 for predicting immune therapy responsiveness in lung cancers are tabulated in FIG. 6; an alternate logistic regression analysis using a sample size of 32 for predicting immune therapy responsiveness in lung cancers are tabulated in FIG. 7, which revealed filter level SSF3 was more statistically significant than other SSF levels for predicting immune response for lung cancers. In this regard, the data was not restricted to tumors located in the lungs but, rather, included all lung cancers regardless of the physical location of the tumor within or outside the lung.

In both sample sizes (14 and 32) the signatures retained only the mean; the remaining metrics (sd, entropy, mpp, skewness, and kurtosis) were not retained in the model. In the analysis shown in FIG. 7, the signature may be expressed as $Y=0.5211+0.008576(x)$, where x is the independent variable and corresponds to the mean value from the QTA. The predictive value of this equation is self-evident; for all mean values greater than (−2.46), there is a greater than 50% probability that the patient is a responder; for all mean values greater than (50.01), there is a greater than 95% probability that the patient is a responder, and so on.

In the analysis shown in FIG. 6, the signature may be expressed as Y=0.4546+0.007114(x), where x corresponds to the mean value from the QTA. The predictive value of this equation is also self-evident, and generally parallels the equation corresponding to FIG. 7.

Both equations suggest that immune responsiveness is most sensitive to the average (or mean) density of pixels within the region of interest for lung cancers.

In various embodiments, it may be desirable to bias the logistic regression analysis in the direction of responders, for example, by using a greater number of responder scans than non-responder scans in the data set. That is, since one objective is to define a responsive signature, it is appropriate to bias the data set to tend towards responders, or else the linkage between responders and the metrics influencing responders may be suppressed or washed out entirely. In various embodiments, the data set may comprise a ration of responders to non-responders in the range of 1:1 to 2:1.

The manner in which the responder population and the non-responder population are defined will now be described in accordance with various embodiments. After evaluating the pixels within an ROI for a scan slice (or group of slices) associated with a particular patient, immune therapy is administered to that patient. Another full volumetric scan is subsequently taken later in time (typically 4 or 8 weeks following introduction of the immune therapy drugs). Based on that subsequent volumetric data, it is determine whether the patient is a responder or a non-responder within the first 8 weeks (this defines an early responder). It remains to determine how to define whether a patient responds to immune therapy.

More particularly, shrinkage in tumor size is an important factor, but not sufficient alone because not all tumors shrink in responders; it is therefore appropriate to also consider changes in the volume and/or density of the tumor. Thus, in one embodiment a responder may be defined as a patient who, in response to immune therapy, experiences a simple reduction in at least 2 of: tumor size, volume, and density.

Moreover, it is known that sometimes tumors may not simply shrink; rather, tumors may exhibit tumor growth kinetics which characterize or define the rate at which the tumor size, volume, and/or density changes over time in the presence of immune therapy. Using a growth kinetics analysis, the mere fact a tumor has shrunk is not enough—it itself—to declare a patient to be a responder. Accordingly, in an alternative embodiment, a responder is conservatively defined where the tumor growth kinetics (in terms of size, volume, and/or density) also trend negative over time. That is, a simple reduction in tumor size is not sufficient to declare the patient a responder; rather, a reduction in tumor size coupled with negative trending growth kinetics (e.g., one, two, or three of a negative growth kinetic for tumor size, volume, and density) is required to conservatively define a responder. Using such a conservative definition for a responder greatly enhances the level of confidence in the predictive value of the signature, because responders which satisfy only the static reduction threshold but who do not also satisfy the kinetic reduction metric are not considered responders.

While the present invention has been described in the context of the foregoing embodiments, it will be appreciated that the invention is not so limited. For example, the various geometric features and chemistries may be adjusted to accommodate additional applications based on the teachings of the present invention.

A biomarker signature is thus provided for use in predicting responsiveness to immune therapy in lung cancer, expressed in the form Y=Mx+B; where Y is a predictive indicator ranging from 0 to 1; B is a constant; M is a coefficient; and x indicates mean pixel density.

In an embodiment, mean pixel density is derived from imaging data associated with a subjectively determined region of interest (ROI) surrounding a lung lesion.

In an embodiment, mean pixel density is a measure of the average pixel density within a cluster of pixels derived from imaging data surrounding a tumor.

In an embodiment, the imaging data comprises one of MRI, US, PET, DEXA, digital mammography, JPEGS, Angiography, SPECT, and gamma camera data.

In an embodiment, the imaging data comprises CT scan data.

In an embodiment, B has a value in the range of 0.1 to 1, and M has a value in the range of 0.001 to 0.1.

In an embodiment, B has a value in the range of 0.4 to 0.6, and M has a value in the range of 0.007 to 0.09.

In an embodiment, B has a value of about 0.5211, and M has a value of about 0.00858.

In an embodiment, the signature is derived using quantitative textural analysis (QTA) and logistic regression analysis on a first population of known responders and a second population of known non-responders.

A method is also provided for predicting responsiveness to immune therapy in lung cancer patients. The method includes: identifying a first population of known responders and a second population of known non-responders; processing imaging data for the first and second populations using quantitative textural analysis (QTA); generating, for each member of both populations, quantitative metrics using the QTA; performing logistic regression on the quantitative metrics for both populations to yield a predictive signature expressed in the form of Y=Mx+B where x comprises mean pixel density; performing QTA on a lung cancer scan for a subsequent patient; comparing the predictive signature to one or more relevant metrics associated with the subsequent patient; and predicting responsiveness to immune therapy for the subsequent patient based on the comparison.

In an embodiment, the imaging data comprises CT scan data; Y is a predictive indicator ranging from 0 to 1; B is a constant having a value in the range of 0.1 to 1; and M is a coefficient having a value in the range of 0.001 to 0.1.

In an embodiment, the step of processing using QTA comprises generating a histogram of the frequencies of occurrence (Y-axis) of pixels within discrete density boundaries (X-axis).

In an embodiment, the step of processing using QTA comprises using a spatial scale filters SSF3.

In an embodiment, the step of generating, for each member of both populations, quantitative metrics using the QTA comprises identifying a region of interest (ROI) surrounding a tumor.

In an embodiment, the first population of known responders is determined based on whether, in response to immune therapy, their corresponding imaging data reflects a simple reduction in at least 2 of: tumor size, tumor volume, and tumor density.

In an embodiment, the first population of known responders is further determined based on whether, in response to immune therapy, a reduction in tumor size coupled with negative trending growth kinetics in at least two of tumor size, tumor volume, and tumor density.

In an embodiment, the first population of known responders is further determined based on whether, in response to immune therapy, a reduction in tumor size coupled with negative trending growth kinetics in each of tumor size, tumor volume, and tumor density.

In an embodiment, the method further includes performing logistic regression on at least one of the following metrics: smoking history, gene mutation load, tumor markers, patient age, and patient gender.

In an embodiment, the quantitative metrics comprise mean pixel density, standard deviation of a histogram curve, mean positive pixel value of the pixels that are in the positive value range, entropy, skewness, and kurtosis.

Computer code is also provided. The computer code is stored in a non-transient medium which and, when executed by a computer processor, performs the steps of: processing imaging data for a first population of responders and a second population of non-responders using quantitative textural analysis (QTA); generating, for each member of both populations, quantitative metrics using the QTA; and performing logistic regression on the quantitative metrics for both populations to yield a predictive signature expressed in the form of Y=Mx+B; where Y is a predictive indicator ranging from 0 to 1; B is a constant; M is a coefficient; and x indicates mean pixel density.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A non-transitory computer-readable medium storing computer code which, when executed by a computer processor, causes the computer processor to perform a method comprising:
   retrieving a biomarker signature for use in predicting responsiveness to immune therapy in lung cancer, the biomarker signature expressed in the form Y=Mx+B, where Y is a predictive indicator ranging from 0 to 1;
   B is a constant;
   M is a coefficient; and
   x is the mean positive pixel (MPP) value associated with imaging data of a lung lesion, wherein the MPP is calculated using a pixel value scale that includes both negative and positive values;
   performing quantitative textural analysis (QTA) on a lung cancer scan of a patient;
   comparing the biomarker signature to one or more relevant metrics derived using the QTA;
   predicting the patient's responsiveness to immune therapy based on the comparison.

2. The non-transitory computer-readable medium of claim 1, wherein MPP is derived from imaging data associated with a subjectively determined region of interest (ROI) surrounding the lung lesion.

3. The non-transitory computer-readable medium of claim 2, wherein the imaging data comprises one of MRI, US, PET, DEXA, digital mammography, JPEGS, Angiography, SPECT, and gamma camera data.

4. The non-transitory computer-readable medium of claim 2, wherein the imaging data comprises CT scan data.

5. The non-transitory computer-readable medium of claim 4, wherein B has a value in the range of 0.4 to 0.6, and M has a value in the range of 0.007 to 0.09.

6. The non-transitory computer-readable medium of claim 4, wherein B has a value of about 0.5211, and M has a value of about 0.00858.

7. The non-transitory computer-readable medium of claim 1, wherein B has a value in the range of 0.1 to 1, and M has a value in the range of 0.001 to 0.1.

8. The non-transitory computer-readable medium of claim 7, wherein the method further comprises deriving the biomarker signature, prior to retrieving the biomarker signature, using QTA and logistic regression analysis on a first population of known responders and a second population of known non-responders.

9. A method of predicting responsiveness to immune therapy in lung cancer, comprising the steps of:
   identifying a first population of known responders and a second population of known non-responders;
   processing imaging data for the first and second populations using quantitative textural analysis (QTA);
   generating, for each member of both populations, quantitative metrics using the QTA;
   performing logistic regression on the quantitative metrics for both populations to yield a predictive signature expressed in the form of Y=Mx+B where x is mean positive pixel (MPP) value associated with imaging data of a lung lesion, and the MPP is calculated using a pixel value scale that includes both negative and positive values;
   performing QTA on a lung cancer scan for a subsequent patient;
   comparing the predictive signature to one or more relevant metrics associated with the subsequent patient; and
   predicting responsiveness to immune therapy for the subsequent patient based on the comparison.

10. The method of claim 9, wherein:
   the imaging data comprises CT scan data;
   Y is a predictive indicator ranging from 0 to 1;
   B is a constant having a value in the range of 0.1 to 1; and
   M is a coefficient having a value in the range of 0.001 to 0.1.

11. The method of claim 10, wherein the step of processing using QTA comprises generating a histogram of the frequencies of occurrence (Y-axis) of pixels within discrete density boundaries (X-axis).

12. The method of claim 9, wherein the step of processing using QTA comprises using a spatial scale filters SSF3.

13. The method of claim 9, wherein the step of generating, for each member of both populations, quantitative metrics using the QTA comprises identifying a region of interest (ROI) surrounding a tumor.

14. The method of claim 9, wherein the first population of known responders is determined based on whether, in response to immune therapy, their corresponding imaging data reflects a simple reduction in at least 2 of: tumor size, tumor volume, and tumor density.

15. The method of claim 14, wherein the first population of known responders is further determined based on whether, in response to immune therapy, a reduction in tumor size coupled with negative trending growth kinetics in at least two of tumor size, tumor volume, and tumor density.

16. The method of claim 15, wherein the first population of known responders is further determined based on whether, in response to immune therapy, a reduction in tumor size coupled with negative trending growth kinetics in each of tumor size, tumor volume, and tumor density.

17. The method of claim 9, wherein performing the logistic regression comprises performing the logistic regression on a combination of at least the quantitative metrics and at least one of the following bioinformatics metrics: smoking history, gene mutation load, tumor markers, patient age, and patient gender.

18. The method of claim 17, wherein the quantitative metrics comprise mean pixel density, standard deviation of a histogram curve, mean positive pixel value of the pixels that are in the positive value range, entropy, skewness, and kurtosis.

19. The method of claim 9, further comprising:
    determining that the subsequent patient is an immune therapy responder based on the subsequent patient's predicted responsiveness to immune therapy exceeding a threshold probability;
    administering immune therapy to the subsequent patient to treat lung cancer based on the subsequent patient's predicted responsiveness to immune therapy exceeding the threshold probability.

20. Computer code stored in a non-transient medium which, when executed by a computer processor, performs the steps of:
    processing imaging data for a first population of responders and a second population of non-responders using quantitative textural analysis (QTA);
    generating, for each member of both populations, quantitative metrics using the QTA; and
    performing logistic regression on the quantitative metrics for both populations to yield a predictive signature expressed in the form of Y=Mx+B; where
    Y is a predictive indicator ranging from 0 to 1;
    B is a constant;
    M is a coefficient; and
    x is mean positive pixel (MPP) value associated with imaging data of a lung lesion, and the MPP is calculated using a pixel value scale that includes both negative and positive values.

* * * * *